Figure 2:
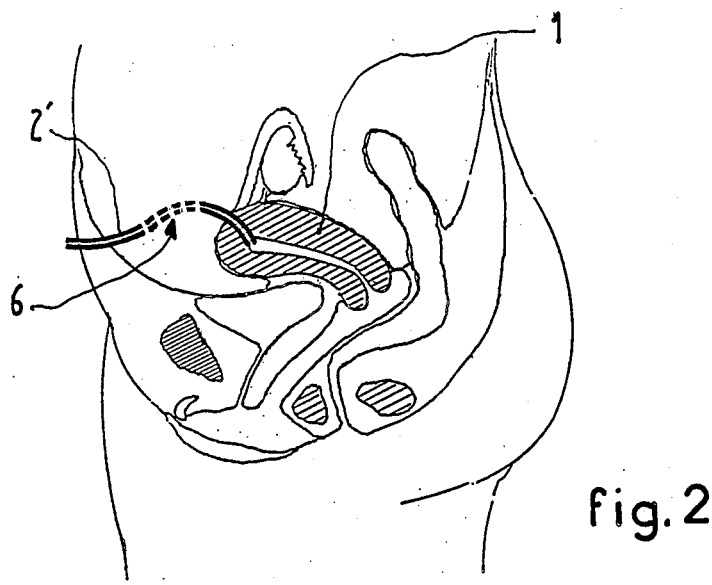

United States Patent [19]

Lenck

[11] Patent Number: 4,832,681

[45] Date of Patent: May 23, 1989

[54] METHOD AND APPARATUS FOR ARTIFICIAL FERTILIZATION

[76] Inventor: Lucien C. Lenck, 34 rue Marechal de Lattre de Tassigny, 63000 Clermont-Ferrand, France

[21] Appl. No.: 127,690

[22] Filed: Dec. 2, 1987

[30] Foreign Application Priority Data

Dec. 10, 1986 [FR] France .............................. 86 17609

[51] Int. Cl.⁴ ..................... A61F 2/04; A61M 25/00
[52] U.S. Cl. ........................................ 600/34; 604/8; 604/55; 604/175; 604/282; 623/12
[58] Field of Search ............. 128/1 R; 623/12; 604/8, 604/55, 174–175, 280, 282

[56] References Cited

U.S. PATENT DOCUMENTS

| | | | |
|---|---|---|---|
| 2,764,975 | 10/1956 | Greenberg | 600/35 |
| 3,618,613 | 11/1971 | Schulte | 604/282 |
| 4,193,392 | 3/1980 | Barnett | 604/175 X |
| 4,491,126 | 1/1985 | Cullor | 604/55 X |
| 4,574,000 | 3/1986 | Hunter | 128/1 R X |
| 4,701,161 | 10/1987 | Lenck | 128/1 R |
| 4,713,074 | 12/1987 | Piacentino | 623/12 |

*Primary Examiner*—Dalton L. Truluck
*Attorney, Agent, or Firm*—Lee C. Robinson, Jr.

[57] ABSTRACT

A method and apparatus for artificial fertilization in which an ovum or embryonic implant is inserted in the uterine cavity by means of tubing which communicates with the outside and passes through the uterine wall. The tubing comprises a flexible but relatively incompressible silicone elastomer tube having, and bulges are provided on the outer surface of the tube. In some embodiments the tube includes a spiral reenforcement of stainless steel wire.

13 Claims, 2 Drawing Sheets

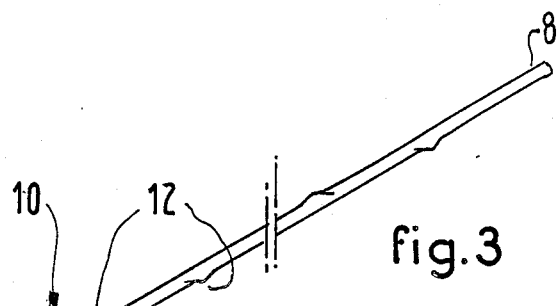
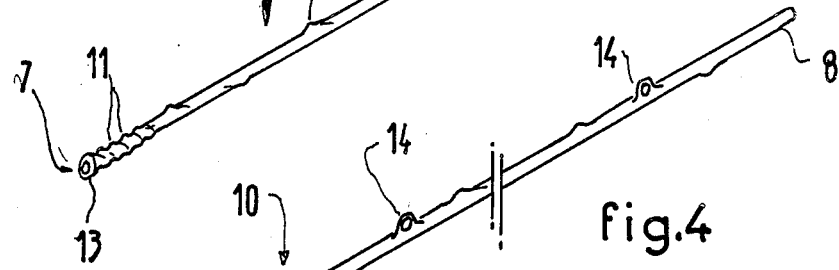
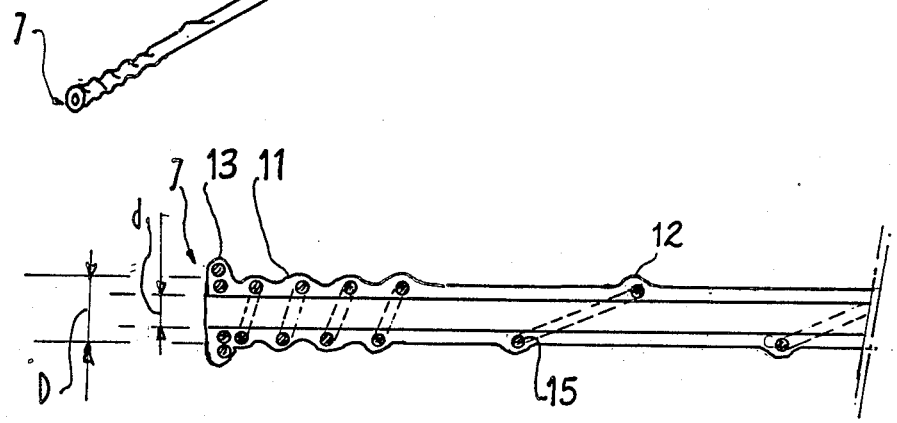
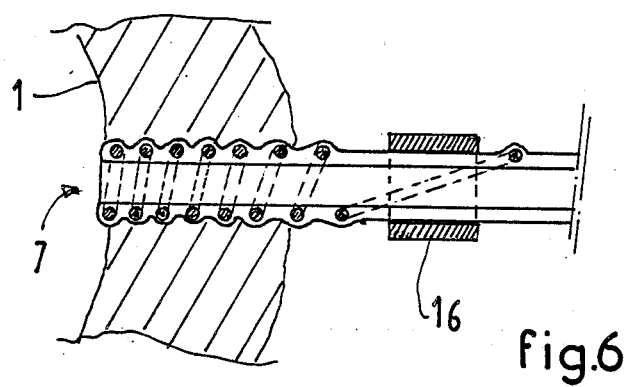

METHOD AND APPARATUS FOR ARTIFICIAL FERTILIZATION

The present invention belongs in the field of so-called artificial fertilization methods, and it relates to an improved fertilization method of the type which consists in implanting an ovum or embryonic material in the uterine cavity for the purpose of causing it to develop therein, as well as to preferred means for carrying out the said method.

The in vitro fertilization method which consists in depositing in a suitable medium either an ovum and spermatozoa or embryonic material is known, the medium being contained in a vessel, flask or test tube maintained under suitable temperature conditions; it is intended that the embryonic material should be transferred fairly quickly to the uterus of the mother or to a so-called surrogate mother; this transfer, performed transcervically, appears to encourage the expulsion of the ovum during prostaglandin-induced uterine contractions. This transfer is, moreover, impossible or difficult in the case of malformations of the neck of the uterus, in the case of a long and irregular endocervical tract (a uterine malformation known as unicorn uterus), and in the case of tight cervical stenosis (following electrocoagulation of the neck, for example).

A method which consists in surrounding the ovary with a sac provided with irrigation channels connected to the outside is also known from a U.S. Pat. No. 4,574,000, the sac opening transtubally into the uterine cavity; this method is awkward on account of the complex operating procedure which it involves (laparotomy) and the uncertain nature of the fertilization as a result of the drainage of the ovary; this method is applicable in the case of malformation or blockage of the Fallopian tubes.

The objective of the present invention is to propose a relatively simple and reliable method for transplantation of the ovum or of embryonic material into the uterine cavity, and it is characterized generally in that it consists in transferring the ovum or the embryonic material into the uterine cavity by means of a tubing material into the uterine cavity by means of a tubing which communicates with the outside and passes through the uterine wall.

Two variants of the method are possible, according to the particular case: a first variant is characterized in that, to reach the uterine wall, the said tubing is passed through the vaginal tract and then in that it is passed through the vaginal wall at the level of the Douglas's cul-de-sac; a second variant is characterized in that to reach the uterine wall, the said tubing is passed transabdominally.

Preferably, the tubing is placed in position during the period of menstruation.

The subject of the present invention is also a device for carrying out a method as defined generally above, this device being characterized generally in that the said tubing consists of a flexible but relatively incompressible tube having an internal diameter of between 2 and 3 mm approximately and an external diameter of between 4 and 45 mm approximately, the said tube incorporating bulges which are fairly pronounced and close together on its outer surface in proximity to at least one of its ends, referred to as the first end.

Preferably, the said tube incorporates more widely spaced bulges along its entire outer surface; also preferably, the said tube incorporates a flange at least at its first end; preferably, finally, the said tube consists essentially of an elastic material which is tolerated by the body, and a spiral reinforcement designed on the one hand to endow the tube with its relative incompressibility and on the other hand to participate in the formation of the said bulges.

Figure 1:
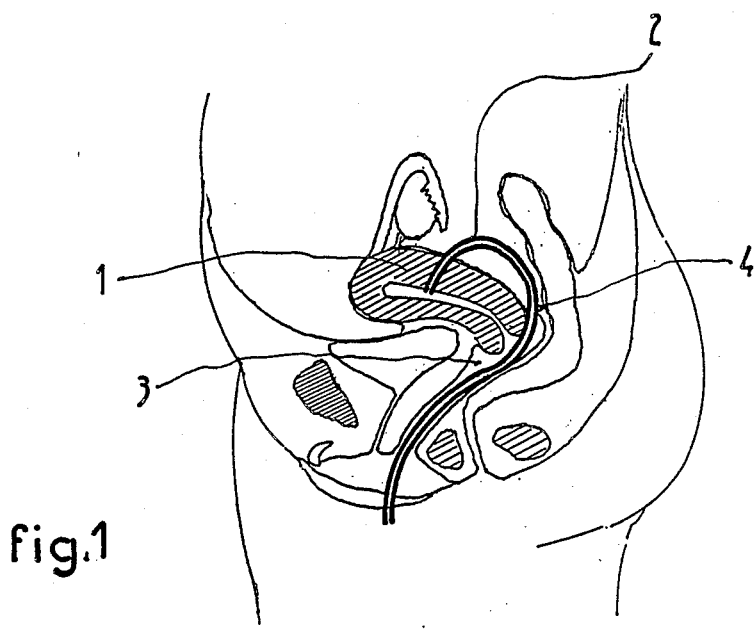

The present invention will be better understood, as regards both the procedure used and the means proposed, from the description of it which will be given with reference to the figures in the attached plates, wherein:

FIG. 1 illustrates the arrangement of a tubing according to the first variant,

FIG. 2 illustrates another arrangement of a tubing according to the second variant, FIG. 3 illustrates in perspective a tubing by means of which either of the variants may be applied, FIG. 4 is a similar illustration of a tubing incorporating accessory arrangements, FIG. 5 is a partial longitudinal section of a tube of the preceding figure, and FIG. 6 is a similar representation of a variant of the tubing of FIG. 5.

FIG. 1 shows in a conventional manner a sagittal section of the female genital system, in which the uterus 1 has been perforated in its median portion to permit the passage of a tubing 2; the tubing 2 opens into the external medium via the vaginal tract 3 after passing through this wall at the level 4 of the Douglas's cul-de-sac.

In FIG. 2, a tubing 2' arrangement differs from the above in that the passage through the uterine wall 1 is made either transtubally or in a transuterine manner in proximity to the uterine fundus, and in that the said tubing is in communication with the external medium via the transabdominal route; a portion 6 of the tubing has been shown in dotted lines to indicate that the tubing is much longer than it appears in the drawing since it will be required to conform to the spatial contours of the pelvic and parietal peritoneum.

In FIG. 3, a tube 10 designed to form a tubing 2 of the preceding figures is distinguished by the fact that it incorporates bulges 11 which are fairly pronounced and close together on its outer face and in proximity to one end, while it incorporates more widely spaced bulges such as 12 over most of its length. It is provided at its end with a flange 13; the end having the bulges 11 and flange 13 is naturally designed to be inserted through a hole made in the uterine wall.

In FIG. 4, a tube similar to the above differs from the latter, however, by the presence of small eyelet loops 14; these eyelets are designed to enable the tube to be attached to tissues of the body.

In FIG. 5, which shows on a larger scale the tube of FIG. 4 in section but which could equally well be applied to the tube of FIG. 3, disregarding the eyelet loops 14, it is seen that the stiffness of the tube made of flexible material, such as silicone elastomer, is imparted by the presence of a spiral reinforcement 15 made of stainless steel wire; the manner in which the turns of the spiral reinforcement contribute to the formation of the bulges 11 and 12 and also contribute, by means of the superposition of two concentric and coplanar turns, to the formation of the flange 13 is clearly seen in the section. The internal diameter d is approximately 2.5 mm and the external diameter D approximately 4.5 mm.

FIG. 6 shows a variant of the tube of the invention inserted at its end into the uterine wall 1; it will be noted that the tube is surrounded by a sleeve 16 situated at a sufficient distance from the end 7 for the sleeve to be at a distance of about ten millimetres from the outer face of the uterine wall. The sleeve is a small Dacron (Registered Trade Mark) cylinder about ten millimetres long; this sleeve, which can be stuck to the tube by means of silicone elastomer, is designed to be colonized by the components of the connective tissue, thereby contributing to maintaining the tubing in position.

In variants not shown in the figures, some intermediate portions of the tube may incorporate closely wound turns of the spiral reinforcement, so as to make these portions stiffer; in other variants, the second end 8 may likewise have closely wound turns of the spiral reinforcement.

It will also be noted in FIGS. 5 and 6 that the internal walls of the tubes are smooth, this being in order to permit the passage of other finer catheters or of various surgical, measuring, observation or sampling instruments. The intubation arrangement according to the invention will prove, in particular, very useful for the purposes of trophoblast sampling designed for an early examination of the karyotype.

Although particular and preferred forms, both of carrying out the method and of embodiment of tubes according to the invention, have been described and shown, it must be understood that these forms do not restrict the scope of the invention, which is defined by the general or detailed characteristics stated above.

I claim:

1. A fertilization method of the type in which an ovum or embryonic implant is inserted in the uterine cavity for the purpose of causing it to develop therein, the method comprising forming a perforation or surgical opening in the uterine wall, inserting a tubing from outside the body through the perforated opening into the uterine cavity and thereafter transferring said implant into the uterine cavity by means of said tubing.

2. A method according to claim 1, characterized in that, to reach the uterine wall, the said tubing is passed transabdominally.

3. A fertilization method of the type in which an ovum or embryonic implant is inserted in the uterine cavity for the purpose of causing it to develop therein, the method comprising transferring the implant into the uterine cavity by means of tubing which communicates with the outside and passes through the uterine wall, to reach the uterine wall the said tubing being passed through the vaginal tract and then being passed through the vaginal wall at the level of the Douglas's cul-de-sac.

4. A method according to claim 3, characterized in that the tubing is placed in position during the period of menstruation.

5. A device for carrying out a fertilization method of the type in which an ovum or embryonic implant is inserted into the uterine cavity comprising a flexible but relatively incompressible tube having an internal diameter of between about 2 and 2.5 mm and an external diameter of between about 4 and 4.5 mm, the said tube incorporating incompressible bulges on its outer surface in proximity to at least one of its ends.

6. A device according to claim 5, characterized in that the bulges on said tube are widely spaced along its entire length.

7. A device according to claim 5, characterized in that the said tube incorporate a flange adjacent said one end.

8. A device according to claim 5, characterized in that the said tube comprises an elastic material, and a spiral reinforcement connected to said tube.

9. A device according to claim 8, characterized in that the said spiral reinforcement comprises stainless steel wire, and in that the said elastic material comprises a silicone elastomer.

10. A device according to claim 5, characterized in that the said tube includes eyelets arranged at intervals on its outer wall.

11. A device according to claim 5 characterized in that the said tube has a length of between about 250 and 350 mm and is designed to be passed transabdominally.

12. A device according to claim 5, characterized in that the said tube has a length of between about 150 and 250 mm and is designed to be passed through the vagina.

13. A device according to claim 5, characterized in that a Dacron sleeve surrounds the tube in proximity to an end of the tube.

* * * * *